(12) United States Patent
Czaplewski et al.

(10) Patent No.: US 12,740,887 B2
(45) Date of Patent: Sep. 22, 2026

(54) OSTOMY APPLIANCE AND FILTER ASSEMBLY WITH BYPASS VENTING

(71) Applicant: Hollister Incorporated, Libertyville, IL (US)

(72) Inventors: Gregory J. Czaplewski, Glendale Heights, IL (US); Patrick C. Tetzlaff, Caledonia, WI (US); Brian T. Leadingham, Pleasant Prairie, WI (US); Alex J. Gruber, Wind Lake, WI (US); Nicholas A. Kerscher, Oak Creek, WI (US)

(73) Assignee: HOLLISTER INCORPORATED, Libertyville, IL (US)

( * ) Notice: Subject to any disclaimer, the term of this patent is extended or adjusted under 35 U.S.C. 154(b) by 688 days.

(21) Appl. No.: 17/766,681

(22) PCT Filed: Oct. 12, 2020

(86) PCT No.: PCT/US2020/055244
§ 371 (c)(1),
(2) Date: Apr. 5, 2022

(87) PCT Pub. No.: WO2021/091658
PCT Pub. Date: May 14, 2021

(65) Prior Publication Data

US 2024/0065876 A1 Feb. 29, 2024

Related U.S. Application Data

(60) Provisional application No. 62/933,064, filed on Nov. 8, 2019.

(51) Int. Cl.
*A61F 5/441* (2006.01)

(52) U.S. Cl.
CPC ...... *A61F 5/441* (2013.01); *A61F 2005/4415* (2013.01)

(58) Field of Classification Search
CPC .............. A61F 5/441; A61F 2005/4415; A61F 5/4405; A61F 5/4404; A61F 5/4407; A61F 5/445; A61F 5/451
See application file for complete search history.

(56) References Cited

U.S. PATENT DOCUMENTS 4,211,224 A * 7/1980 Kubach .................. A61F 5/441
604/333
5,306,264 A * 4/1994 Ferguson ............... A61F 5/441
604/338

(Continued)

FOREIGN PATENT DOCUMENTS

EP 0116363 A1 8/1984
EP 1101462 A1 5/2001

(Continued)

OTHER PUBLICATIONS

International Search Report issued by ISA/EPO in connection with PCT/US2020/055244 on Dec. 18, 2020.

(Continued)

*Primary Examiner* — Adam Marcetich
*Assistant Examiner* — Arjuna P Chatrathi
(74) *Attorney, Agent, or Firm* — Klintworth & Rozenblat LLP

(57) ABSTRACT

An ostomy appliance (10) includes a pouch wall (12) defining at least a portion of a collection chamber (14) configured to collect and store effluent from a stoma, an inlet (16) formed in the pouch wall configured to be secured around the stoma, and a filter assembly (110) having a filter (114), a valve (116) and a bypass venting chamber (112) extending between the filter and the valve. The filter includes an active gas inlet section (124) configured to (Continued)

receive gas from the collection chamber, a bypass gas inlet section (126) configured to receive gas through the valve, and a filter outlet section (118) for exiting gas to the atmosphere.

10 Claims, 6 Drawing Sheets

(56) References Cited

U.S. PATENT DOCUMENTS 5,693,035 A * 12/1997 Leise, Jr. ................ A61F 5/441 604/332
6,135,986 A * 10/2000 Leisner ................ A61F 5/441 604/324
6,659,988 B1 * 12/2003 Steer ................ A61F 5/441 604/335
6,659,998 B2 * 12/2003 DeHoogh ........... A61F 9/00736 606/4
7,341,578 B2 * 3/2008 Bulow ................ A61F 5/441 604/338
2003/0236509 A1 * 12/2003 Silvestrini ............... A61F 5/441 604/332
2005/0070863 A1 * 3/2005 Bulow ................ A61F 5/441 604/338
2008/0275410 A1 * 11/2008 Burt ................ A61F 5/441 604/333
2013/0072886 A1 * 3/2013 Schertiger ............... A61F 5/445 604/335
2013/0085463 A1 * 4/2013 Lesko ................ A61F 5/441 604/333

FOREIGN PATENT DOCUMENTS

WO 2006127124 A1 11/2006
WO 2012062322 A1 5/2012

OTHER PUBLICATIONS

European Search Report for application No. EP23214035.0 mailed on Apr. 4, 2024, 8 Pages.
International Preliminary Report on Patentability issued by ISA/EPO in connection with PCT/US2020/055244 on May 10, 2022.

* cited by examiner

OSTOMY APPLIANCE AND FILTER ASSEMBLY WITH BYPASS VENTING

BACKGROUND

The following description relates to an ostomy appliance, for example, an ostomy pouch having a filter assembly with bypass venting.

Known ostomy bags include a filter arranged at a wall of the bag to vent and deodorize gas from inside the bag to the atmosphere. However, the filter may become partially or completely occluded, for example, by effluent within the bag. An occluded filter may restrict venting of the gas through the filter and pressure may accumulate in the bag. This may lead to undesirable ballooning of the bag.

Accordingly, it is desirable to provide an ostomy appliance, such as an ostomy pouch, having a filter assembly configured to provide for bypass venting of gas to the atmosphere.

SUMMARY

In one embodiment, an ostomy appliance includes a pouch wall defining at least a portion of a collection chamber configured to collect and store effluent from a stoma, an inlet formed in the pouch wall configured to be secured around the stoma and a filter assembly including filter, a valve and a bypass venting chamber extending between the filter and the valve. The filter includes an active gas inlet section configured to receive gas from the collection chamber, a bypass gas inlet section configured to receive gas through the valve, and a filter outlet section for exiting gas to the atmosphere.

In one embodiment, the valve may be operable between a closed configuration in which gas flow from the collection chamber to the bypass venting chamber through the valve is restricted, and an open configuration in which the collection chamber and the bypass venting chamber are in fluid communication with one another such that gas may be received in the bypass venting chamber from the collection chamber through the valve. In one embodiment, the valve may be a check valve. In one embodiment, the valve may include a resilient valve body and a flow control portion movable between a closed condition corresponding to the closed configuration of the valve and an open condition corresponding to the open configuration of the valve. In one embodiment, the valve body may urge the flow control portion to the closed condition. In one embodiment, the filter maybe at least partially disposed in the bypass venting chamber. In one embodiment, the bypass venting chamber may include at least a portion of the pouch wall. In one embodiment, the filter may include hydrophobic membrane.

Other objects, features, and advantages of the disclosure will be apparent from the following description, taken in conjunction with the accompanying sheets of drawings, wherein like numerals refer to like parts, elements, components, steps, and processes.

DETAILED DESCRIPTION

Figure 1:
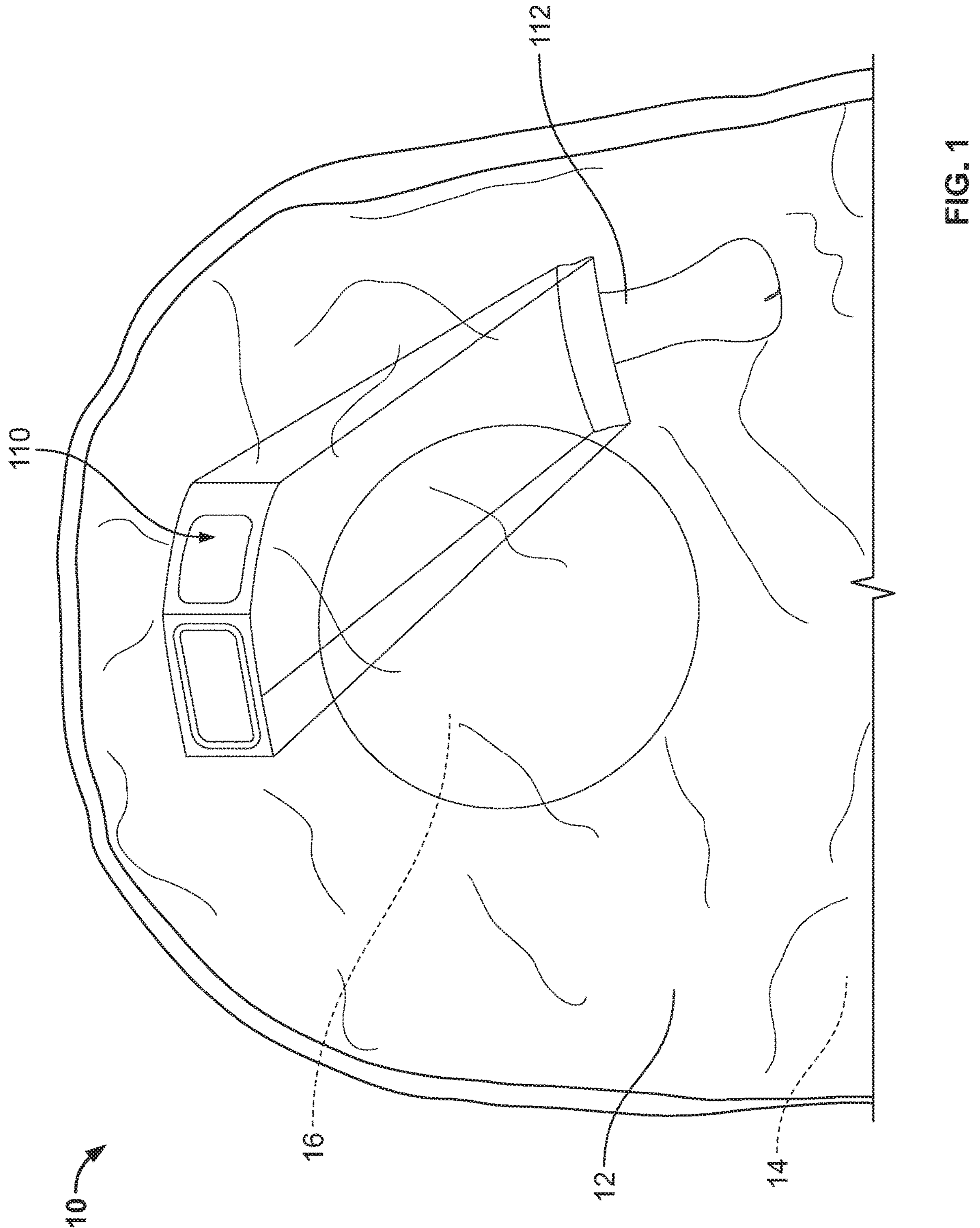
FIG. 1 is a plan view showing a portion of an ostomy appliance having a filter assembly with bypass venting according to an embodiment.

While the present disclosure is susceptible of embodiment in various forms, there is shown in the drawings and will hereinafter be described one or more embodiments with the understanding that the present disclosure is to be considered illustrative only and is not intended to limit the disclosure to any specific embodiment described or illustrated.

FIG. 1 is a plan view showing a portion of an ostomy appliance 10 having a filter assembly 110 with a bypass venting chamber 112, according to an embodiment. The ostomy appliance 10 may be an ostomy pouch configured to be secured to a user in a known manner. The ostomy appliance 10 includes a pouch wall 12 defining at least a portion of a collection chamber 14 within the ostomy appliance 10 configured to receive and store effluent discharged from a stoma. A stoma inlet opening 16 is formed in the pouch wall 12 and is configured to be fitted around the stoma when the ostomy appliance is secured to the user.

Figure 2:
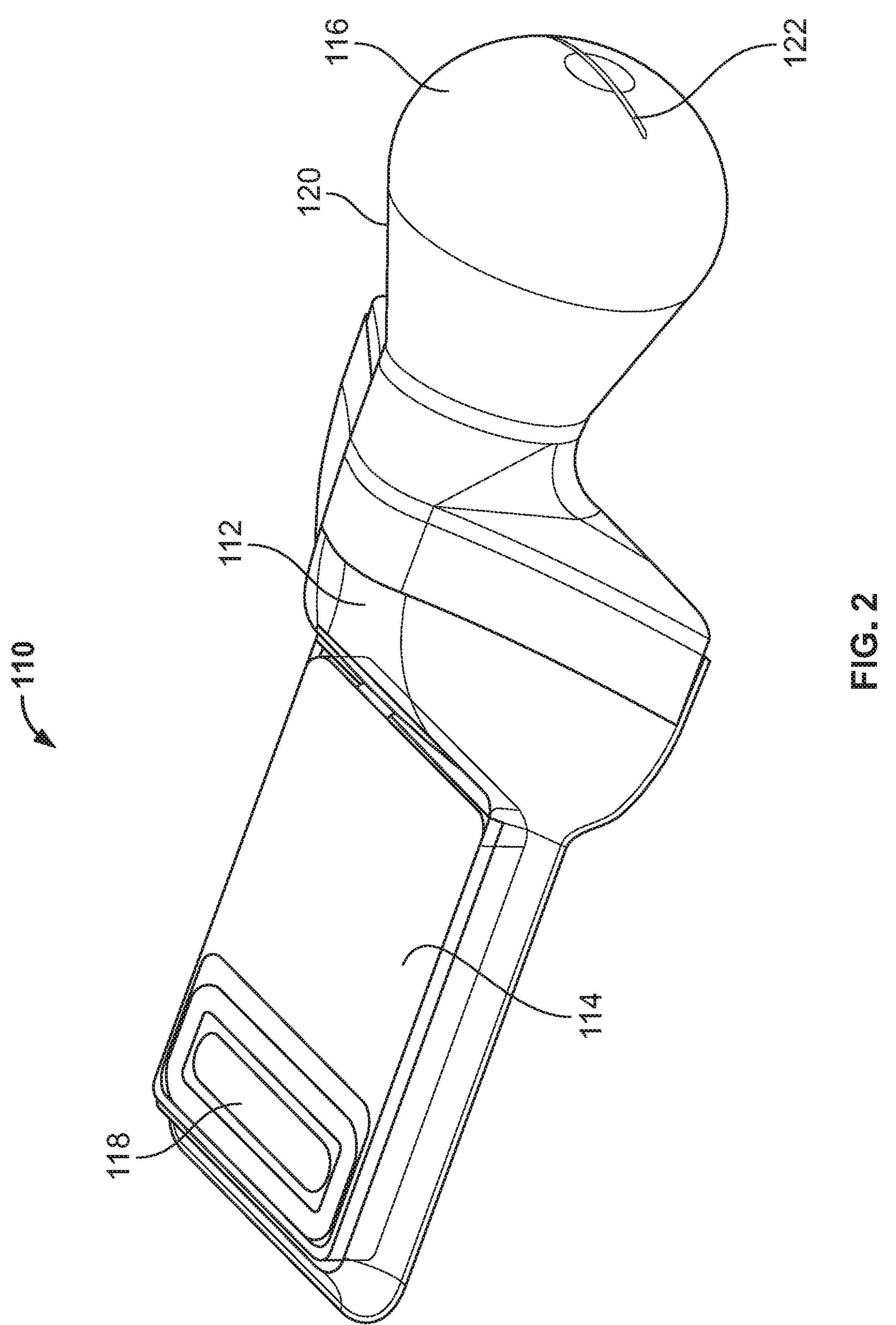
FIG. 2 is a perspective view of the filter assembly with bypass venting according to an embodiment.
Figure 3:
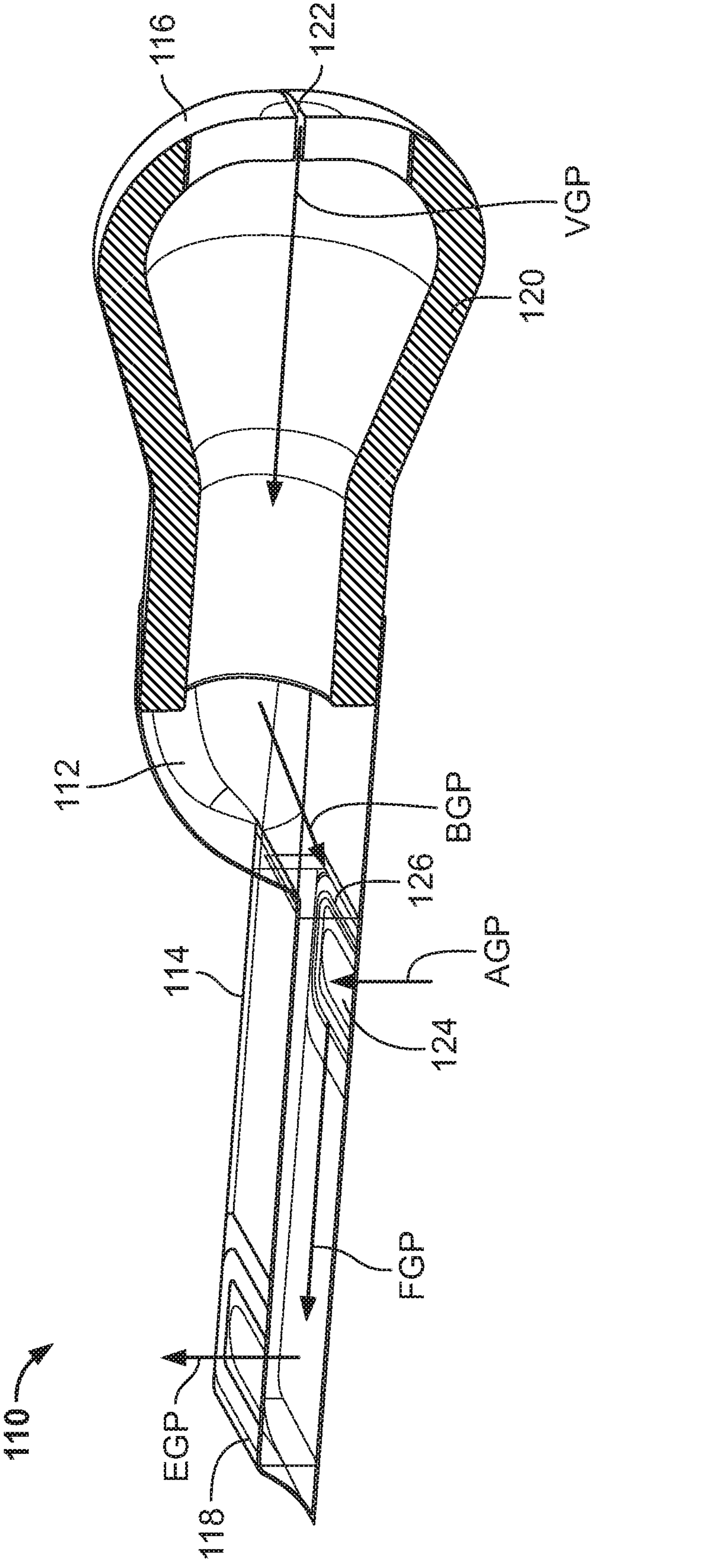
FIG. 3 is a cross-sectional side view of the filter assembly with bypass venting according to an embodiment.

FIG. 2 is a perspective view of the filter assembly 110 according to an embodiment. FIG. 3 is a cross-sectional side view of the filter assembly 110 according to an embodiment. The filter assembly 110 includes a filter 114 and a valve 116 fluidically connected to one another by the bypass venting chamber 112. The bypass venting chamber 112 may be formed, for example, by a housing, barrier, membrane or other similar structure connected to and extending between the filter 114 and the valve 116. In one embodiment, at least a portion of the bypass venting chamber 112 may be formed by the pouch wall 12.

In one embodiment, the filter 114 may be a porous, gas-permeable filter configured to deodorize a gas flowing through the filter 114. Examples of such filters include known carbon filters commonly used in ostomy appliances. The filter 114 may include a hydrophobic membrane so that the filter 114 is substantially liquid impermeable. In one embodiment, the filter 114 may be at least partially disposed in the bypass venting chamber 112. The filter 114 includes a filter outlet section 118 through which a filtered gas may exit and be released to the atmosphere.

The valve 116 includes a valve body 120 and a flow control portion 122 configured to be operated between a closed condition and an open condition. In one embodiment, the valve 116 may be a check valve. In one embodiment, the valve body 120 may be a substantially resilient body, and the flow control portion 122 may be a valve slit formed in the valve body 120.

Referring to FIG. 3, the filter 114 further includes an active gas inlet section 124 and a bypass gas inlet section 126. The filter 114 is configured to receive unfiltered gas from the collection chamber 14 through the active gas inlet section 124. The filter 114 is also configured to receive unfiltered gas from the bypass venting chamber 112 through the bypass gas inlet section 126.

The valve 116 is operable between a closed configuration in which flow of unfiltered gas from the collection chamber 14 into the bypass venting chamber 112 through the valve

116 is substantially prevented, and an open configuration in which flow of unfiltered gas from the collection chamber 14 into the bypass venting chamber 112 through the valve is permitted. In one embodiment, the valve 116 may be actuated, i.e., moved from the closed configuration to the open configuration, by applying a force to the valve body 120, for example, by manually squeezing the valve body 120, by a gas pressure within the collection chamber 14, or by a specific actuating tool on the valve 116 or a tool configured for use with the valve 116. In one embodiment, the valve 116 may be moved from the open configuration to the closed configuration by a applying a force in a direction opposite to that described above for moving the valve to the open configuration. In one embodiment, the valve 116 may be resiliently urged to one of the open configuration or the closed configuration such that the valve 116 is normally open or normally closed.

In one embodiment, the valve body 120 is a bulb-shaped portion made of a resilient material and the flow control portion 122 is a valve slit resiliently urged to a closed condition, corresponding to the closed configuration of the valve 116. A force, such as a manual squeezing force, may be applied to the valve body 120 to move the valve 116 to the open configuration by moving the flow control portion 122 to the open condition. The valve 116 may be returned to the closed configuration by releasing the squeezing force, allowing the flow control portion 122 to return to the closed condition under the resiliency of the valve body 120.

It will be appreciated that the present disclosure is not limited to the example described above and shown in FIGS. 2 and 3. For example, the force applied to the valve 116 may be a one-way directional force, for example, from a gas pressure in the collection chamber 14. The valve body 120 may elastically deform to move the flow control portion 122 to the open condition if the force exceeds a predetermined value. The flow control portion 122 may return to the closed condition when the force, e.g., gas pressure, in the collection chamber 14 falls below the predetermined value.

The filter assembly 110 may be installed or formed in the ostomy appliance 10 at the pouch wall 12. According to one embodiment, in an active venting state, unfiltered gas in the collection chamber 14 flows toward the filter 114 along active gas path AGP and is received in the filter 114 through the active gas inlet section 124. The gas may then flow through the filter 114 along filter gas path FGP where the gas is filtered (i.e., deodorized). The filtered gas may then exit the filter 114 through the filter outlet section 118 to the atmosphere along exit gas path EGP.

Occlusion of the active gas inlet section 124 of the filter 114 by effluent in the collection chamber 14 may restrict flow of gas into the filter 114 through the active gas inlet section 124 and cause gas pressure to accumulate in the collection chamber 14. To vent gas from the collection chamber 14, the valve 116 may be actuated to the open configuration so that the bypass venting chamber 112 is in fluid communication with, and receives unfiltered gas from, the collection chamber 14 through the valve 116. For example, with the valve 116 in the open configuration, i.e., with the flow control portion 122 in the open condition, the unfiltered gas from the collection chamber 14 may flow through the flow control portion 122 into the valve 116 along valve gas path VGP. The unfiltered gas may then flow into the bypass venting chamber 112 to the filter 114 along bypass gas path BGP, and into the filter 114 through the bypass gas inlet section 126. The gas may then flow through the filter 114 along the filter gas path FGP and exit the filter 114 through filter outlet section 118 to the atmosphere along the exit gas path EGP in the manner described above.

Accordingly, in the examples above, undesirable gas pressure in the ostomy appliance 10 resulting from an occluded filter inlet section may be substantially relieved or avoided by operation of the valve 116, which allows unfiltered gas to bypass the occluded section of the filter 114.

Figure 4:
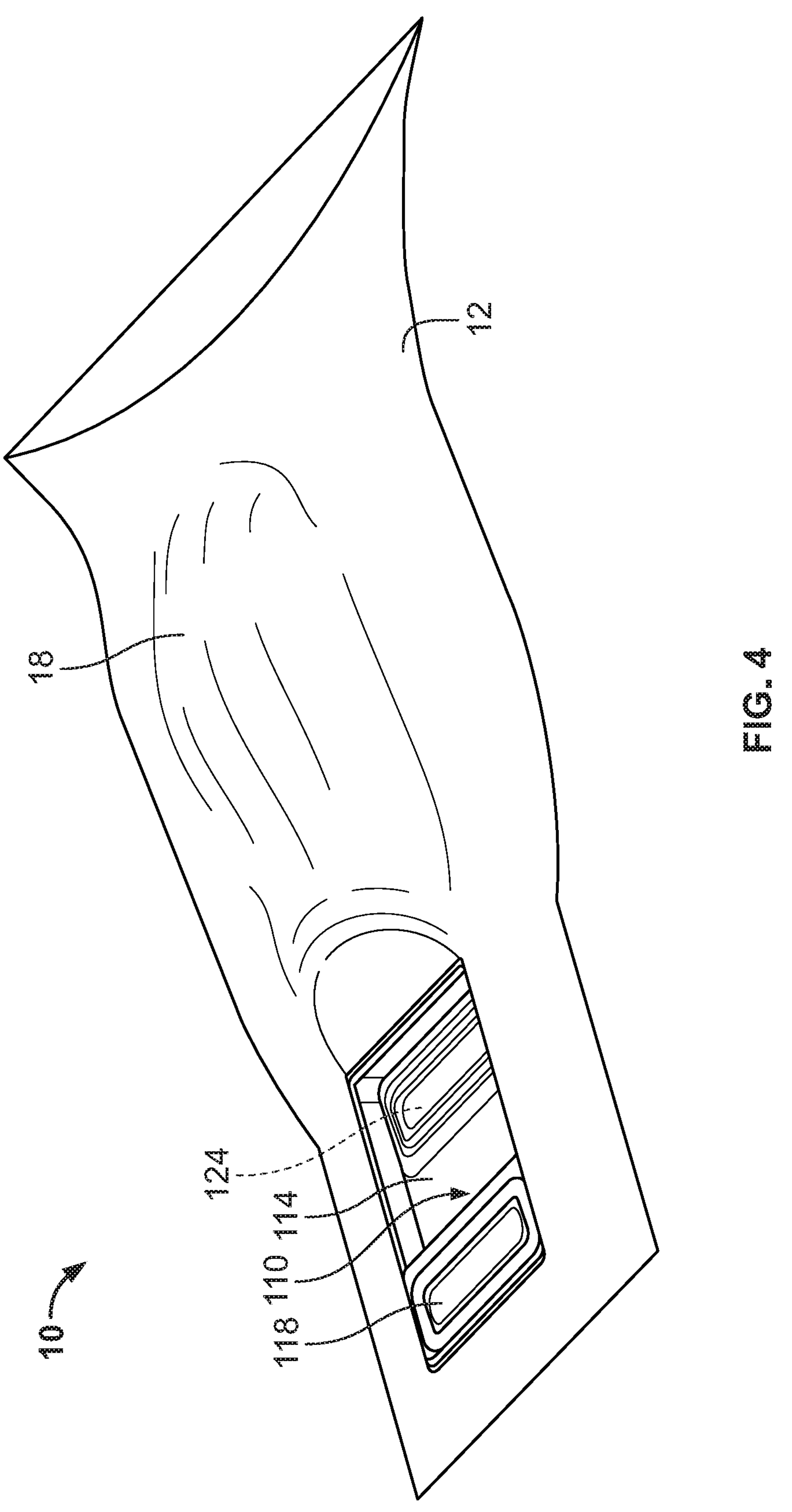
FIG. 4 is a perspective view of an ostomy appliance having a filter assembly with bypass venting according to an embodiment.
Figure 5:
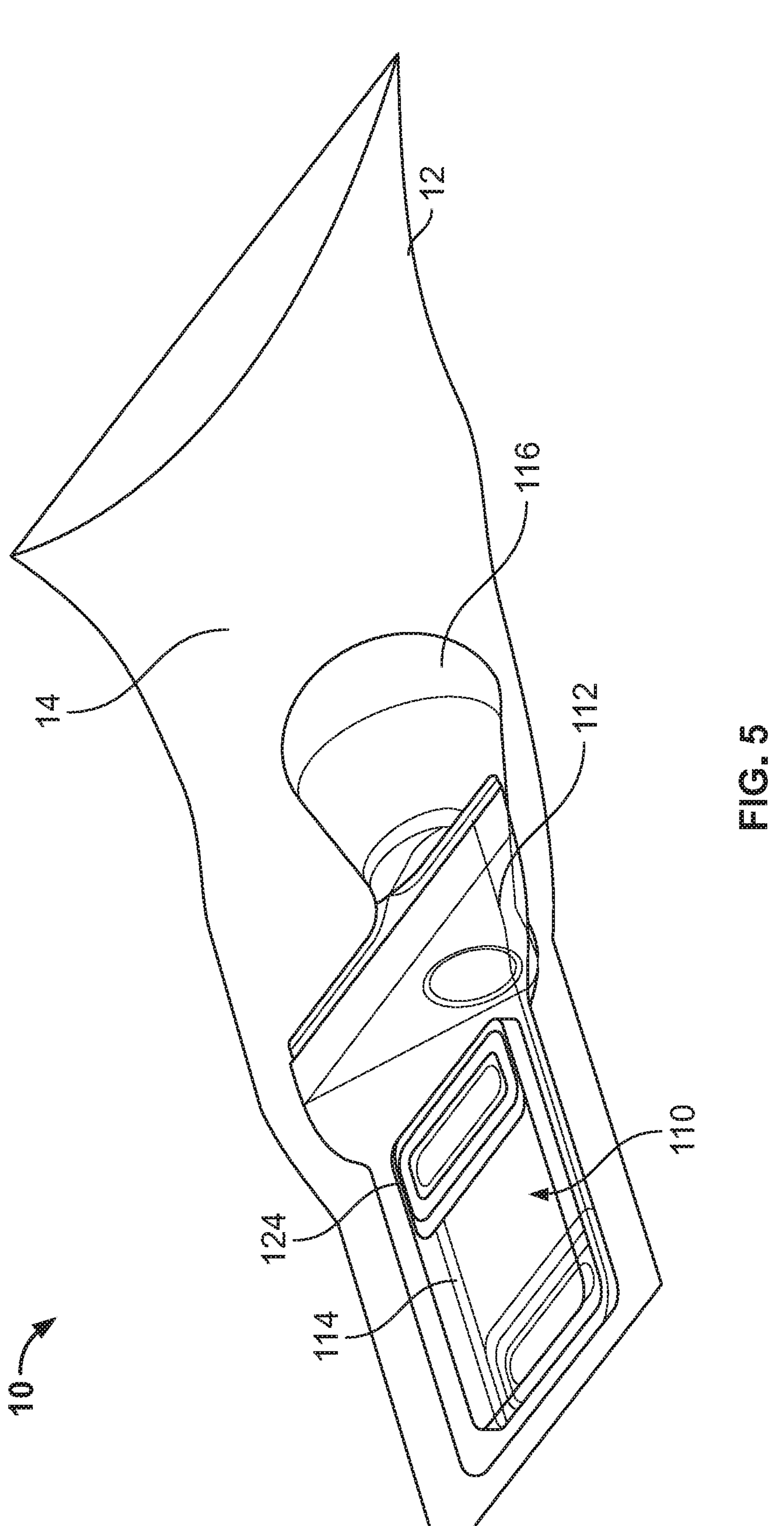
FIG. 5 is a cut-away perspective view showing an interior of an ostomy appliance having a filter assembly with bypass venting according to an embodiment.

FIG. 4 is a perspective view of an outer surface of the ostomy appliance 10 having the filter assembly 110 according to an embodiment. FIG. 5 is a cut-away perspective view showing an interior of the ostomy appliance 10 having the filter assembly 110 according to an embodiment. In one embodiment, the filter assembly 110 is disposed relative to the pouch wall 14 such that at least the bypass venting chamber 112 and the valve 116 are disposed within the pouch wall 14. Thus, in one embodiment, the valve 116 may be operated by applying a force to pouch wall 14 in the vicinity of the valve body 120 such that the force is transmitted to the valve body 120. For example, as shown in FIG. 4, a force may be applied to a first section 18 on an outer surface of the pouch wall 12 to actuate the valve 116.

Figure 6:
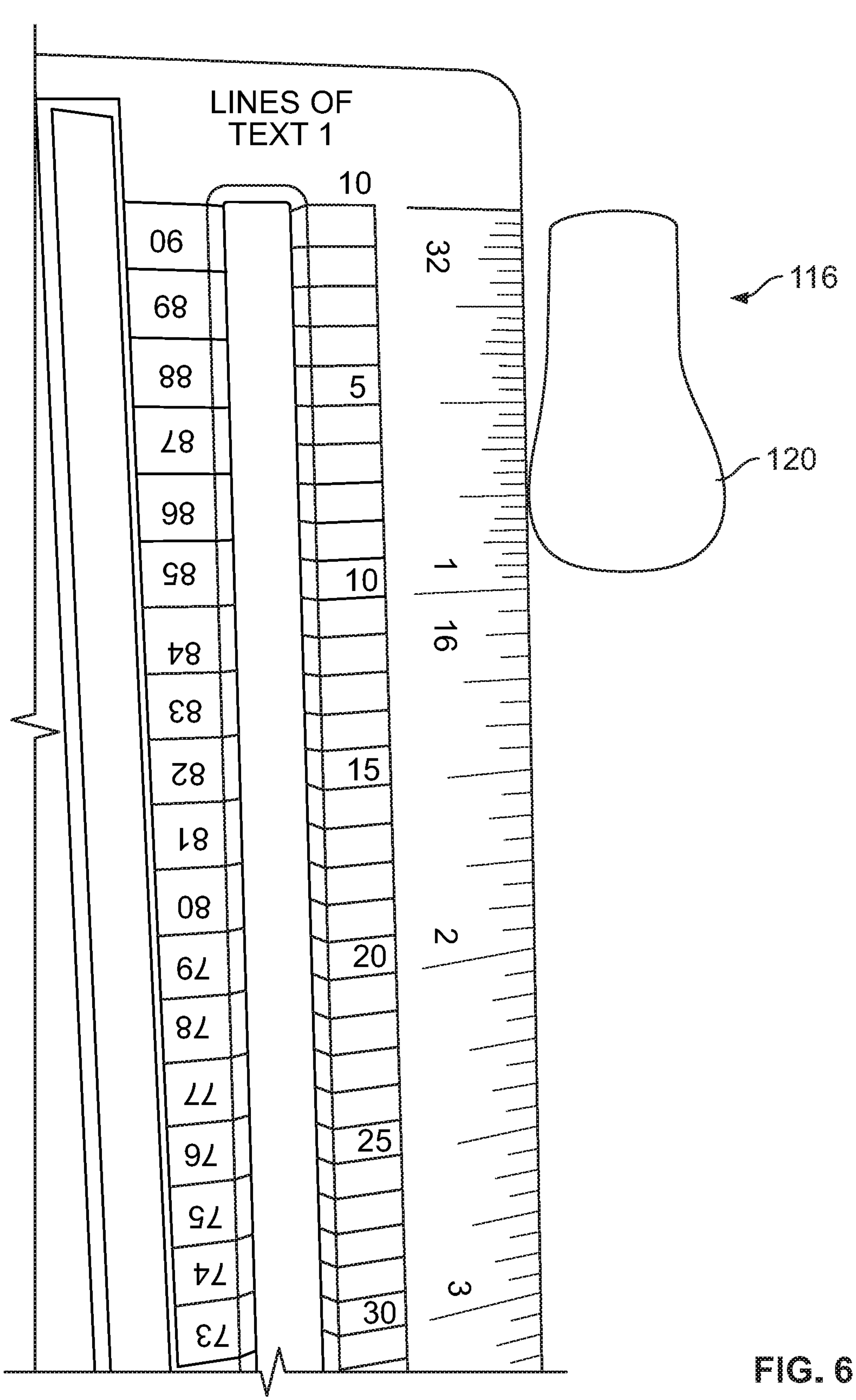
FIG. 6 shows an example of a valve for use with a filter assembly having bypass venting according to an embodiment.

FIG. 6 shows the valve 116, including a valve body 120 formed as a bulb-shaped portion, according to an embodiment.

In some embodiments, the filter assembly 110 may include a bulb check valve 116. Active venting of gas from inside the ostomy appliance to the atmosphere may be accommodated through a filter having a hydrophobic membrane. The filter assembly 110 may include a bypass of the interior hydrophobic membrane in case of occlusion. In an embodiment, the bypass may be performed by manual operation of the valve 116. In this manner, gas may be vented through the filter along different path to bypass the occluded section.

In an alternate embodiment, the filter assembly 110 may include portions of the pouch wall 12, i.e., pouch surfaces. The pouch surfaces 12 may be specifically contoured for each of access to operate the valve 116, for example, to squeeze the bulb portion. The filter assembly may be attached to the ostomy appliance using known techniques, e.g., heat sealing.

It is understood that the relative directions described above, e.g, "upward," "downward," "upper," "lower," "above," "below," are used for illustrative purposes only and may change depending on an orientation of the ostomy pouch and/or the patient. Accordingly, this terminology is non-limiting in nature. In addition, it is understood that one or more various features of an embodiment above may be used in, combined with, or replace other features of a different embodiment described herein.

All patents referred to herein, are hereby incorporated herein in their entirety, by reference, whether or not specifically indicated as such within the text of this disclosure.

In the present disclosure, the words "a" or "an" are to be taken to include both the singular and the plural. Conversely, any reference to plural items shall, where appropriate, include the singular.

From the foregoing it will be observed that numerous modifications and variations can be effectuated without departing from the true spirit and scope of the novel concepts of the present invention. It is to be understood that no limitation with respect to the specific embodiments illustrated is intended or should be inferred. The disclosure is intended to cover by the appended claims all such modifications as fall within the scope of the claims.

The invention claimed is:

1. An ostomy appliance comprising:

a pouch wall defining at least a portion of a collection chamber configured to collect and store effluent from a stoma;

an inlet formed in the pouch wall configured to be secured around the stoma; and a filter assembly comprising: a filter, a valve and a bypass venting chamber extending between the filter and the valve, wherein the valve comprises:

a closed configuration in which gas flow from the collection chamber to the bypass venting chamber through the valve is restricted; and an open configuration in which the collection chamber and the bypass venting chamber are in fluid communication with one another such that gas is received in the bypass venting chamber from the collection chamber through the valve, wherein the filter comprises:

an active gas inlet section configured to receive gas from the collection chamber;

a bypass gas inlet section configured to receive gas from the bypass venting chamber, wherein gas enters the bypass venting chamber from the collection chamber through the valve in the open configuration, and wherein the active gas inlet section is at a different location on the filter from the bypass gas inlet section; and a filter outlet section for exiting gas to the atmosphere, and wherein, in an active venting state, the filter assembly is configured to allow gas from the collection chamber to flow toward the filter through the active gas inlet section and through the filter to exit the filter through the filter outlet section with the valve in the closed configuration, and wherein the filter extends from the bypass venting chamber to the filter outlet section.

2. The ostomy appliance of claim 1, wherein the valve is a check valve.

3. The ostomy appliance of claim 1, wherein the valve comprises a resilient valve body and a flow control portion movable between a closed condition corresponding to the closed configuration of the valve and an open condition corresponding to the open configuration of the valve.

4. The ostomy appliance of claim 3, wherein the resilient valve body urges the flow control portion to the closed condition.

5. The ostomy appliance of claim 1, wherein the filter is at least partially disposed in the bypass venting chamber.

6. The ostomy appliance of claim 1, wherein the bypass venting chamber includes at least a portion of the pouch wall.

7. The ostomy appliance of claim 1, wherein the filter includes a hydrophobic membrane.

8. The ostomy appliance of claim 1, wherein when the active gas inlet section becomes occluded, actuating the valve transitions the valve from the closed configuration to the open configuration allowing gas from the collection chamber to flow toward the filter through the bypass gas inlet section.

9. The ostomy appliance of claim 8, wherein actuating the valve is configured to occur based on a pressure in the collection chamber causing a force on the valve to exceed a predetermined threshold causing the valve to actuate move from the closed configuration to the open configuration.

10. The ostomy appliance of claim 9, wherein the valve is configured to move from the open position to the closed position based on the force dropping below the threshold due to the pressure in the collection chamber decreasing.

* * * * *